US009220580B2

(12) United States Patent
Borovinskih et al.

(10) Patent No.: US 9,220,580 B2
(45) Date of Patent: Dec. 29, 2015

(54) DETERMINING A DENTAL TREATMENT DIFFICULTY

(75) Inventors: Artem Borovinskih, San Jose, CA (US); Roman A. Roschin, Moscow (RU); Rene M. Sterental, Palo Alto, CA (US); Dmitriy Ten, Novosibirsk (RU)

(73) Assignee: Align Technology, Inc., San Jose, CA (US)

( * ) Notice: Subject to any disclaimer, the term of this patent is extended or adjusted under 35 U.S.C. 154(b) by 706 days.

(21) Appl. No.: 13/410,182

(22) Filed: Mar. 1, 2012

(65) Prior Publication Data

US 2013/0231900 A1 Sep. 5, 2013

(51) Int. Cl.
*G06F 17/50* (2006.01)
*A61C 7/00* (2006.01)

(52) U.S. Cl.
CPC .................................... *A61C 7/002* (2013.01)

(58) Field of Classification Search
None
See application file for complete search history.

(56) References Cited

U.S. PATENT DOCUMENTS

2002/0042038 A1* 4/2002 Miller et al. .................... 433/24
2007/0003907 A1* 1/2007 Chishti et al. .............. 433/217.1
2010/0145664 A1* 6/2010 Hultgren et al. .................. 703/1
2010/0196837 A1* 8/2010 Farrell .............................. 433/6
2011/0207072 A1* 8/2011 Schiemann ....................... 433/9

* cited by examiner

*Primary Examiner* — Omar Fernandez Rivas
*Assistant Examiner* — Bernard E Cothran
(74) *Attorney, Agent, or Firm* — Brooks, Cameron & Huebsch, PLLC

(57) ABSTRACT

Embodiments for determining a dental treatment difficulty are described herein. One method embodiment includes receiving an initial and subsequent position of each of a first tooth and a second tooth and calculating a change in position of each of the first tooth and the second tooth. The method embodiment can also include projecting the changes in position of each of the first tooth and the second tooth onto a reference line and calculating a change in position on the reference line for the first tooth and the second tooth. The method embodiment can further include determining the dental treatment difficulty based on the changes in position on the reference line.

20 Claims, 4 Drawing Sheets

230

RECEIVING AN INITIAL AND SUBSEQUENT POSITION OF EACH OF A FIRST TOOTH AND A SECOND TOOTH — 202

CALCULATING A CHANGE IN POSITION OF EACH OF THE FIRST TOOTH AND THE SECOND TOOTH — 204

PROJECTING THE CHANGES IN POSITION OF EACH OF THE FIRST TOOTH AND THE SECOND TOOTH ONTO A REFERENCE LINE — 206

CALCULATING AN AVERAGE CHANGE IN POSITION ON THE REFERENCE LINE FOR THE FIRST TOOTH AND THE SECOND TOOTH — 208

DETERMINING THE DENTAL TREATMENT DIFFICULTY BASED ON THE AVERAGE CHANGES IN POSITION ON THE REFERENCE LINE — 212

DETERMINING A DENTAL TREATMENT DIFFICULTY

TECHNICAL FIELD

The present disclosure relates to systems and methods for determining a dental treatment difficulty.

BACKGROUND

The present disclosure relates generally to the field of dental treatment. More specifically, the present disclosure relates to determining a treatment difficulty.

Some objectives in the field of dental treatment are to realign a patient's teeth to positions where the teeth function well and/or align the teeth to provide a pleasing aesthetic appearance. One goal of a treatment provider can be to take the patient's dentition from a starting arrangement to a final arrangement. In such processes, treatment providers may need to correct a patient's anterior-posterior movement within a quadrant of teeth.

For many treatment providers, knowing how difficult a treatment will be can be useful in dental treatment planning. For example, it can indicate to a treatment provider the length of treatment, what dental appliances may be needed, and/or whether the treatment professional has the proper training and/or is capable of treating the patient.

DETAILED DESCRIPTION

Figure 1A:
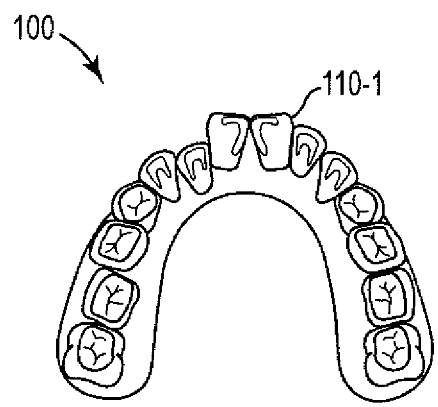
FIG. 1A illustrates an initial virtual dental model according to one or more embodiments of the present disclosure.

Embodiments of the present disclosure include computing device related, system, and method embodiments for determining dental treatment difficulty. For example, one or more method embodiments include, receiving an initial and subsequent position of each of a first tooth and a second tooth and calculating a change in position of each of the first tooth and the second tooth. One or more method embodiments can also include projecting the changes in position of each of the first tooth and the second tooth onto a reference fine and calculating a change in position on the reference line for the first tooth and the second tooth. One or more method embodiments can further include determining the dental treatment difficulty based on the changes in position on the reference line.

In the following detailed description of the present disclosure, reference is made to the accompanying drawings that form a part hereof, and in which is shown by way of illustration how a number of embodiments of the disclosure may be practiced. These embodiments are described in sufficient detail to enable those of ordinary skill in the art to practice a number of embodiments of this disclosure, and it is to be understood that other embodiments may be utilized and that changes may be made without departing from the scope of the present disclosure.

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate the embodiments of the present disclosure, and should not be taken in a limiting sense. As used herein, "a", "at least one", "a number of" something can refer to one or more such things.

Anterior-posterior (A-P) correction is a movement of teeth in a quadrant (e.g., upper left, upper right, lower left, lower right) when movements of teeth in a segment of the quadrant between a first molar and a canine, along an arch are all in a distal direction (e.g., toward the last tooth in a quadrant of a dental arch) or all in a mesial direction (e.g., direction toward an anterior midline in a dental arch). Estimating a treatment difficulty of A-P correction can, as discussed above, aid in predicting and/or adjusting a treatment plan of a patient.

Based on root movement measurements, an amount of mesial and/or distal movement of canine and posterior teeth for a quadrant can be calculated for a patient. Having average mesial and/or distal movement of a posterior tooth and a canine, based on prior completed dental treatments on other patients, as well as a table of treatment difficulty ranges can allow for estimating a level of treatment difficulty for a quadrant of teeth. This level and the calculated value of A-P correct can be presented to a treatment provider for use in treatments and treatment planning.

In various embodiments, with the use of computer graphic software, a treatment professional can establish a custom treatment target specific to a particular tooth of a particular patient. With this treatment target in mind, a dental treatment difficulty can be determined.

Virtual dental models from a scan of a patient's dentition can be provided with computer-aided tooth-treatment systems. An initial digital data set (IDDS) representing an initial tooth arrangement may be obtained in a variety of ways.

For example, the patient's teeth may be imaged to obtain digital data using direct and/or indirect structured light, X-rays, three-dimensional X-rays, lasers, destructive scanning, computer-aided tomographic images or data sets, magnetic resonance images, intra-oral scanning technology, photographic reconstruction, and/or other imaging techniques. The IDDS can include an entire mouth tooth arrangement, some, but not all teeth in the mouth, and/or it can include a single tooth.

A positive model and/or negative impression of the patient's teeth or a tooth may be scanned using an X-ray, laser scanner, destructive scanner, structured light, and/or other range acquisition system to produce the IDDS. The data set produced by the range acquisition system may be converted to other formats to be compatible with the software which is used for manipulating images within the data set, as described herein.

Referring now to FIG. 1A, there is illustrated an initial dental model 100 (e.g., an initial virtual dental model) according to one or more embodiments of the present disclosure. As described herein, the initial dental model 100 can be obtained prior to treatment or at an intermediate state of treatment (e.g., before treatment has been completed).

One or more embodiments of the present disclosure include receiving a virtual IDDS and a desired position of a tooth contained in the virtual IDDS. The initial dental model 100 (e.g., virtual IDDS) can also include a model of an individual tooth (e.g., tooth 110-1) that is part of a full dental model, such as full dental model 100.

Figure 1B:
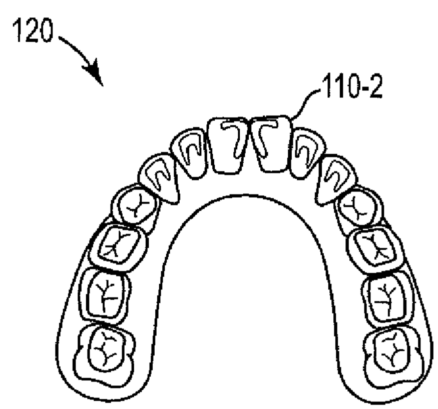
FIG. 1B illustrates a target virtual dental model corresponding to the initial virtual dental model illustrated in FIG. 1A according to the present disclosure.

FIG. 1B illustrates a target dental model 120 (e.g., a target virtual dental model) corresponding to the initial dental model illustrated in FIG. 1A according to the present disclosure. The target dental model 120 can be created by modifying the initial dental model 100 according to one or more treatment goals.

The one or more treatment goals can be case-specific (e.g., specific to the particular patient on which the initial dental model 100 was based). A target dental model can also include a target model of an individual tooth (e.g., tooth 110-2) that is part of a full dental model similar to full target dental model 120. In some embodiments, a virtual IDDS and a target virtual dental model can be displayed via a user interface in three dimensions.

Manual visual estimation of a patient's teeth can also be used in collecting information regarding an initial dental model and target dental model. For example, a treatment provider may take manual measurements of the patient's dentition or one or more particular teeth when determining a difficulty of a particular dental treatment.

Figure 2:
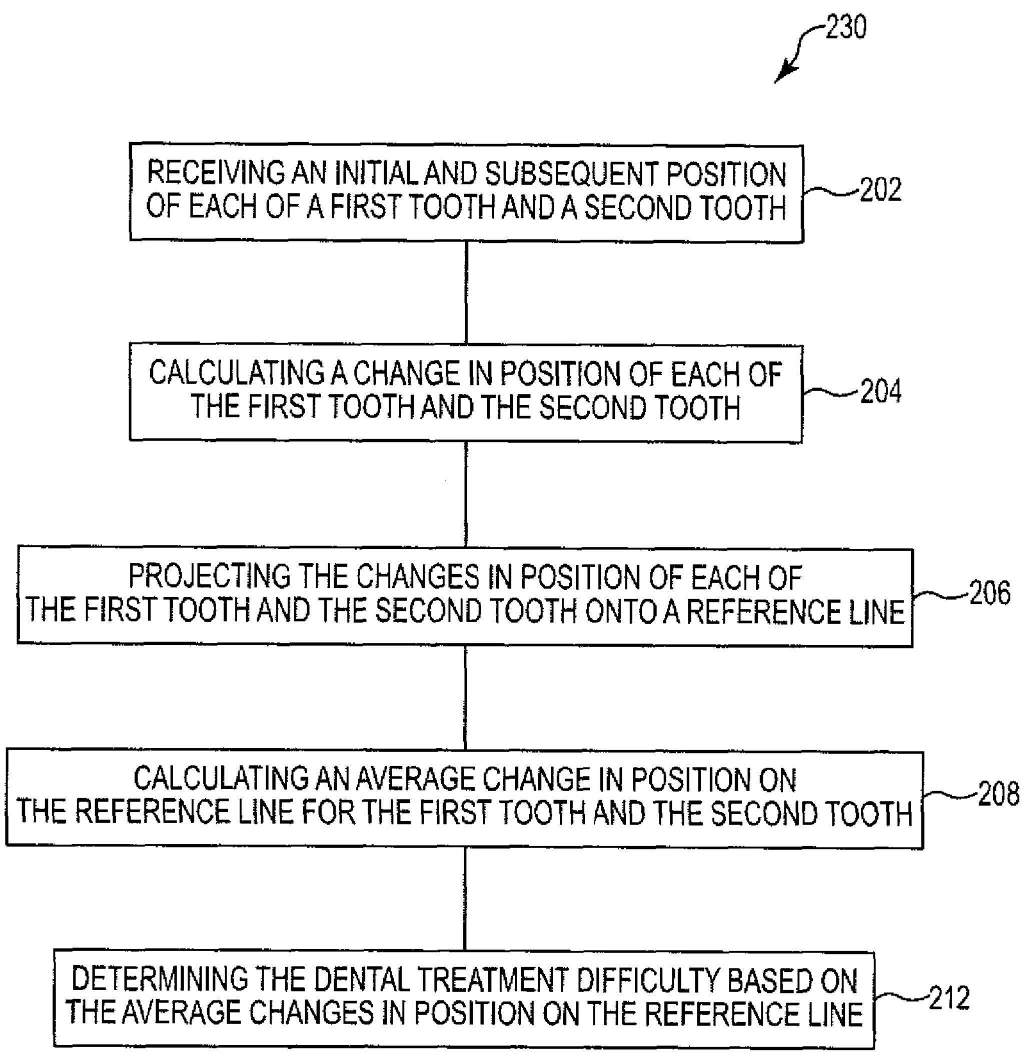
FIG. 2 illustrates an example method for determining a dental treatment difficulty according to one or more embodiments of the present disclosure.

FIG. 2 illustrates an example method 230 for determining a dental treatment difficulty according to one or more embodiments of the present disclosure. At 202, an initial and subsequent position of each of a first tooth and a second tooth is received.

In various embodiments, the first tooth may be a canine tooth, and the second tooth may be a posterior tooth (e.g., a molar). The initial tooth position can be a current tooth position of a patient, and the subsequent position can be a desired tooth position. For example, a patient and his or her treatment provider may plan to have the patient's teeth aligned to a particular desired position.

At 204, a change in position of each of the first tooth and the second tooth is calculated. The changes in position can include mesial and/or distal position changes. For example, calculating the changes in position can include changes along an x and/or y axis, but not a z axis.

The distance between a center point of a tooth (e.g., the first and/or second tooth) in an initial position and a center point of the tooth in a subsequent position may be determined when calculating a change in position, and calculating the changes in position can further include calculating root movement measurements of the first tooth (e.g., canine tooth) and the second tooth (e.g., posterior tooth). For example, based on root movement measurements, an amount (e.g., an average amount) of mesial and/or distal movement of the first and second teeth in a quadrant can be calculated. This amount can be compared to one or more thresholds to determine an amount of A-P correction, as will be discussed further herein.

The changes in position of each of the first tooth and the second tooth can be projected onto a reference line (e.g., an arch line) at 206. For instance, the center point of the tooth (e.g., the first and/or second tooth) at its initial and subsequent positions can be projected onto the reference line.

For example, using the change in position (e.g., distance) between the initial and subsequent position of the tooth, as well as the reference line, a perpendicular projection can be made onto the reference line from the center of the subsequent tooth position. This will be discussed further herein with reference to FIG. 3.

At 208, an average change in position on the reference line for the first tooth and the second tooth is calculated. The average change in position can include adding the change in position between initial and subsequent positions of the first tooth to the change in position between initial and subsequent positions of the second tooth, and dividing the total by two. For example, if the change in position of the first tooth is 4.0 millimeters, and the change in position of the second tooth is 5.0 millimeters, the average change in position is 4.0 mm+5.0 mm/2=4.5 mm.

The dental treatment difficulty is determined at 212 based on the average changes in position on the reference line. The determined dental treatment difficulty can represent an estimation of treatment difficulty of A-P correction, and the results can be presented as a difficulty level and/or quantity.

For example, difficulty levels may be assigned colors to, for example, aid the treatment professional in discerning the level of difficulty. For instance, a difficulty level "black" can include an average change in position from a reference line of 4.0 millimeters or more.

This may be a higher level than a "blue" difficulty level that includes an average change in position of 2.0 to 4.0 millimeters. "Blue" may be a higher treatment difficulty level than "green," which may include an average change in position of 1.0 to 2.0 millimeters. In some such embodiments, an average change in position of less than one millimeter may receive no color label.

In some embodiments, determining the dental treatment difficulty may include comparing the average change in position of the first and second teeth to a threshold change in position. For example, if the threshold change in position is 4.0 millimeters, and the calculated average change in position is greater than 4.0 millimeters, then there is A-P correction movement in the quadrant containing the first and second teeth. If the calculated average change in position is less than the threshold 4.0 millimeters, there is no A-P correction movement in the quadrant containing the first and second teeth. An amount of A-P correction can be determined using this information.

A determination regarding whether to adjust a dental treatment plan can also be made based on the threshold comparison. For example, if an original treatment plan was based on an assumption of A-P correction movement in the quadrant, but it is determined that the calculated average change in position is less than a threshold, the original treatment plan may be changed. This may occur, for example, if it is determined that the treatment plan is too difficult, for instance, for a recommended treatment provider to perform.

In some embodiments, a determined dental treatment difficulty can be compared to a table of difficulty ranges to determine a level of difficulty for a quadrant of teeth, among other benefits. For example, using average mesial and/or distal movement of first and second teeth, as well as a table of treatment difficulty ranges, an estimate of the level of difficulty of treatment for a quadrant of teeth can be determined. This difficulty level and/or a calculated value of A-P correction can be presented to a treatment provider. The dental treatment difficulty level may govern the type of treatment provided to a patient and/or the treatment professional recommended to perform the treatment, as well as the length of treatment.

A determination regarding whether to adjust the dental treatment plan can be made based on a comparison of the dental treatment difficult to a treatment provider skill level. For example, a treatment provider may have certain abilities and/or a certain level of skill that allows for him or her to provide a particular level of treatment (e.g., at or below a certain treatment difficulty level). A treatment provider's skill level may be determined, for example, by a self-ranking, a test score and/or performance, and/or a rating by an appliance provider.

If the provider's skill level does not meet or exceed the determined treatment difficulty level, the provider may not be able to perform the treatment. However, the dental treatment plan may be adjusted based on the comparison, or a different treatment professional may be recommended.

For example, the patient and the provider may choose to alter the treatment in order for it to fall into the provider's skill level. For instance, dental treatment difficulty, a type of dental treatment, and/or a duration of dental treatment may be adjusted based on the adjusted dental treatment plan.

Figure 3:
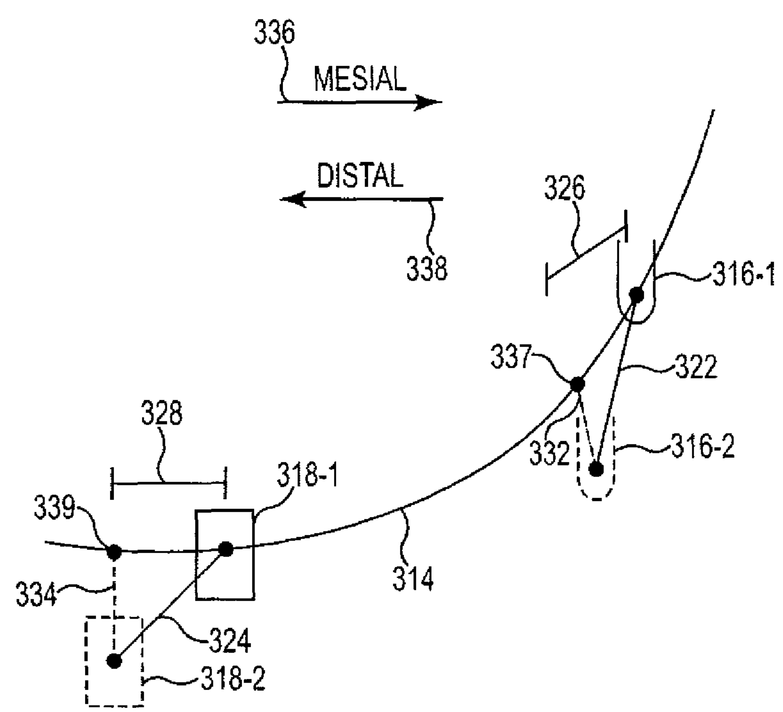
FIG. 3 illustrates an example of changes in position of teeth on a reference line according to one or more embodiments of the present disclosure.

FIG. 3 illustrates an example of changes in position of teeth on a reference line 314 according to one or more embodiments of the present disclosure. In an example, reference line 314 can be an arch line.

As indicated by arrows 336 and 338, respectively, teeth can move in mesial and distal directions. In the example illustrated in FIG. 3, a first tooth (e.g., canine tooth) has an initial mouth position at 316-1 and a subsequent position at 316-2.

The distance between the center of the tooth at its initial position 316-1 and its subsequent position 316-2 is indicated by vector 322. The center of the tooth at its initial position 316-1 is located on reference line 314, while the center of the tooth at its subsequent position 316-2 is located some distance 332 from reference line 314.

The projected change in position of the first tooth from initial position 316-1 to subsequent position 316-2 can be projected onto reference line 314 at point 337. Point 337 can be located a distance 326 along reference line 314 from the center point of the initial position 316-1.

In the example illustrated in FIG. 3, a second tooth (e.g., posterior tooth) has an initial mouth position at 318-1 and a subsequent position at 318-2. The distance between the center of the tooth at its initial position 318-1 and its subsequent position 318-2 is indicated by vector 324.

The center of the tooth at its initial position 318-1 is located on reference line 314, while the center of the tooth at its subsequent position 318-2 is located some distance 334 from reference line 314. The projected change in position of the first tooth from initial position 318-1 to subsequent position 318-2 can be projected onto reference line 314 at point 339. Point 339 can be located a distance 328 along reference line 314 from the center point of the initial position 318-1.

Figure 4:
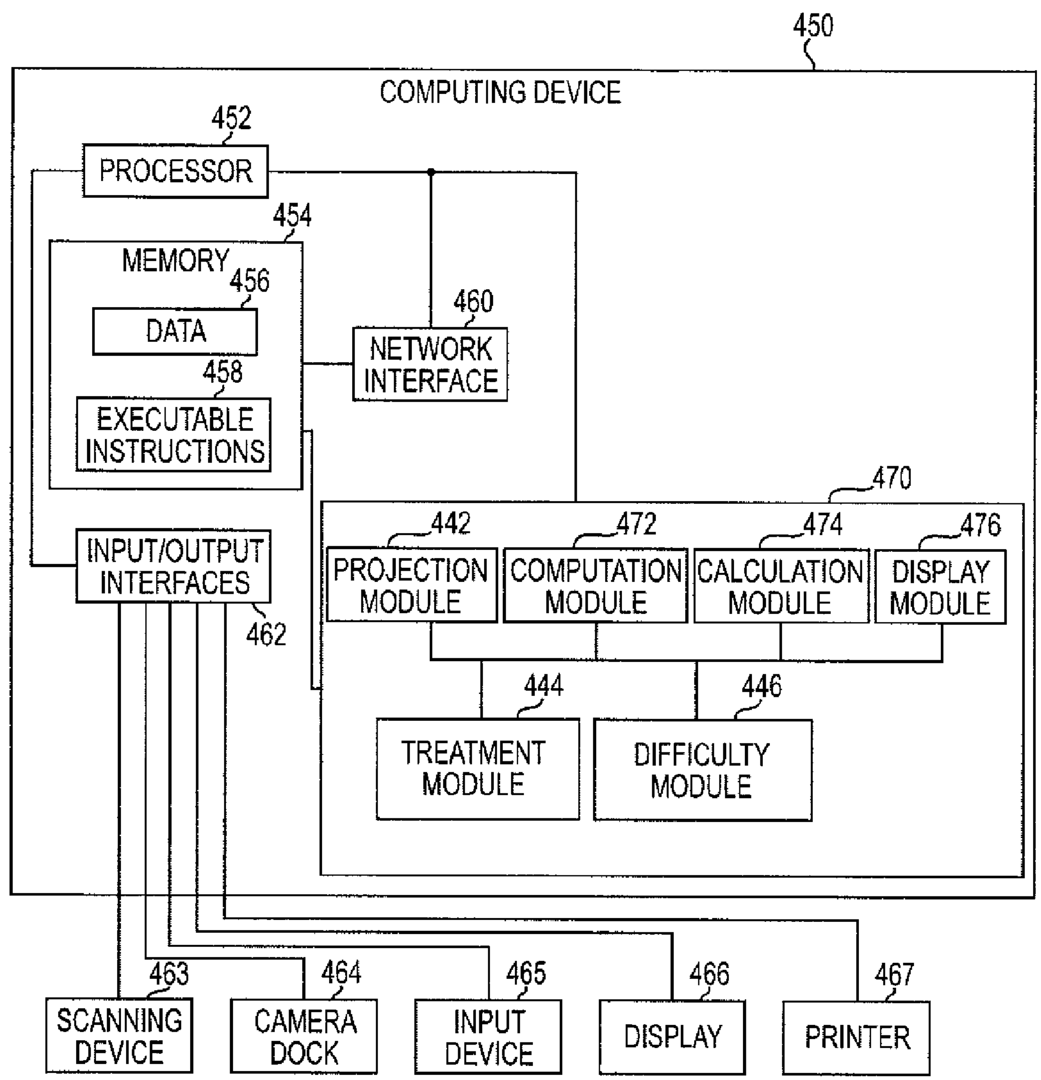
FIG. 4 illustrates an example system for determining a dental treatment difficulty according to one or more embodiments of the present disclosure.

In the example illustrated in FIG. 3, the first tooth can be a canine, and the second tooth can be a first molar. The use of the canine and the first molar as reference may be beneficial, for example, because spacing of each of one or more teeth between the canine and the first molar can be captured FIG. 4 illustrates an example system for determining a dental treatment difficulty according to one or more embodiments of the present disclosure. In the system illustrated in FIG. 4, the system includes a computing device 450 having a number of components coupled thereto. The computing device 450 includes a processor 452 and memory 454. The memory can include various types of information including data 456 and executable instructions 458, as discussed herein.

Memory and/or the processor may be located on the computing device 450 or off the device, in some embodiments. As such, as illustrated in the embodiment of FIG. 4, a system can include a network interface 460. Such an interface can allow for processing on another networked computing device, can be used to obtain information about the patient, and/or can be used to obtain data and/or executable instructions for use with various embodiments provided herein.

As illustrated in the embodiment of FIG. 4, a system can include one or more input and/or output interfaces 462. Such interfaces can be used to connect the computing device with one or more input and/or output devices.

For example, in the embodiment illustrated in FIG. 4, the system can include connectivity to a scanning device 463, a camera dock 464, an input device 465 (e.g., a keyboard, mouse, etc.), a display device 466 (e.g., a monitor), a printer 467, and/or one or more other input devices 465. The input/output interlace 462 can receive executable instructions and/or data, storable in the data storage device (e.g., memory 454), representing a digital dental model of a patient's dentition and/or initial and subsequent positions of a first tooth (e.g., a canine) and second tooth (e.g., a posterior tooth).

In some embodiments, the scanning device 463 can be configured to scan one or more physical molds of a patient's dentition. In one or more embodiments, the scanning device 463 can be configured to scan the patient's dentition directly. The scanning device 463 can be configured to input data into the computing device wherein the data can be provided to the application modules 470.

In some embodiments, the camera dock 464 can receive an input from an imaging device (e.g., a two-dimensional or three-dimensional imaging device) such as a digital camera, a printed photograph scanner, or other suitable imaging device. The input from the imaging device can, for example, be stored in memory 454.

The processor 452 can execute instructions to provide a visual indication of a treatment plan and/or dental treatment difficulty on the display 466. The computing device 450 can be configured to allow a treatment professional or other user to input treatment goals. Input received can be sent to the processor 452 as data and/or can be stored in memory 454.

Such connectivity can allow for the input and/or output of data and/or instructions among other types of information. Although some embodiments may be distributed among various computing devices within one or more networks, such systems as illustrated in FIG. 4, can be beneficial in allowing for the capture, calculation, and/or analysis of information discussed herein.

The processor 452, in association with the data storage device (e.g., memory 454), can be associated with data and/or application modules 470. The processor 452, in association with the memory 454, can store and/or utilize data and/or execute instructions to provide a number of application modules for determining a dental treatment difficulty. As used herein, a module can be a stand alone program or portion of a program or can be a set of code that provides a particular functionality and may not be stand alone and may not even include instructions interspersed within a set of code.

Application modules can include a computation module 472, a calculation module 474, a projection module 442, a treatment module 444, a difficulty module 446, and/or a display module 476.

Computation module 472 can, for example, be configured to compute a change in position between an initial position and a subsequent position of each of a first (e.g., canine) and second (e.g., posterior) tooth. Projection module 442 can be configured to project the changes in position for each of the first and second tooth onto a reference line, and calculation module 474 can be configured to calculate an average change in position of the first tooth and second tooth in relation to the reference line.

Difficulty module 446 can be configured to determine the dental treatment difficulty based on the average change in position, and treatment module 444 can be configured to adjust a dental treatment plan based on a comparison of the dental treatment difficulty and a provider skill level. Difficulty module 446 can be further configured to determine the dental treatment difficulty based on a calculated A-P correction dental treatment plan. Display module 476 can be configured to display a change in position of the first tooth and a change in position of the second tooth, the projected changes, the average change in position, the dental treatment difficulty, and/or the adjusted dental treatment plan.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

The invention claimed is:

1. A computing device implemented method of determining a dental treatment difficulty, comprising: using a computing device to perform: receiving an initial and subsequent position of each of a first tooth and a second tooth;

calculating a change in position of a point on each of the first tooth and the second tooth at the initial position and a point on each of the first tooth and the second tooth at the subsequent position;

projecting the changes in position of each of the first tooth and the second tooth from the initial to the subsequent position onto a reference line;

calculating an average change in position on the reference line for the first tooth and the second tooth;

and determining the dental treatment difficulty of the initial to subsequent position based on the average change in position on the reference line.

2. The method of claim 1, wherein the first tooth is a canine tooth.

3. The method of claim 1, wherein the second tooth is a posterior tooth.

4. The method of claim 1, wherein determining the dental treatment difficulty includes comparing the change in position to a threshold change in position.

5. The method of claim 4, further comprising determining whether to adjust a dental treatment plan based on the comparison.

6. The method of claim 1, wherein the first tooth has a center point and wherein the point on the first tooth used to calculate a change in position is the center point of the tooth.

7. The method of claim 1, wherein a type of dental treatment to be performed is determined based on the determined dental treatment difficulty.

8. The method of claim 1, wherein a duration of dental treatment to be performed is determined based on the determined dental treatment difficulty.

9. The method of claim 1, further comprising determining whether to adjust a dental treatment plan based on a comparison of the dental treatment difficulty to a treatment provider skill level.

10. A non-transitory computer-readable medium having executable instructions that can be executed by a processor to cause a computing device to perform a method of determining a dental treatment difficulty, comprising:

receiving an initial position of a canine tooth and an initial position of a posterior tooth;

receiving a subsequent position of the canine tooth and a subsequent position of the posterior tooth;

calculating a change in position of a point on the canine tooth at the initial position and a point on the canine tooth at the subsequent position and a change in position of a point on the posterior tooth at the initial position and a point on the posterior tooth at the subsequent position;

projecting the changes in position of the canine tooth and the posterior tooth from the initial to the subsequent position onto a reference line;

calculating an average change in position on the reference line for the canine tooth and the posterior tooth;

comparing the change in position on the reference line for the canine tooth and the posterior tooth to a threshold change in position; and determining the dental treatment difficulty of the initial to subsequent position based on the comparison of the average change in position on the reference line for the canine tooth and the posterior tooth to the threshold change in position.

11. The non-transitory computer-readable medium of claim 10, wherein determining the dental treatment difficulty includes determining whether to adjust a dental treatment plan based on the comparison.

12. The non-transitory computer-readable medium of claim 10, wherein the reference line is an arch line.

13. The non-transitory computer-readable medium of claim 10, wherein the dental treatment difficulty is compared to a number of difficulty ranges to determine a level of difficulty for a quadrant of teeth.

14. The non-transitory computer-readable medium of claim 10, wherein the change in position is at least one of a change in mesial position and a change in distal position.

15. The non-transitory computer-readable medium of claim 10, wherein calculating the change in position of the canine tooth and a change in position of the posterior tooth includes calculating root movement measurements of the canine tooth and the posterior tooth.

16. A system for determining a dental treatment difficulty, comprising:

a memory having computer-readable instructions stored thereon;

and a processor coupled to the memory to execute the computer-readable instructions to: compute a change in position between an initial position and a subsequent position of each of a canine tooth and a posterior tooth, wherein the change of position is a distance between a point on the canine tooth at the initial position and a point on the canine tooth at the subsequent position and a distance between a point on the posterior tooth at the initial position and a point on the posterior tooth at the subsequent position;

project the changes in position for each of the canine tooth and the posterior tooth from the initial position to the subsequent position onto a reference line;

calculate an average change in root position of the canine tooth and the posterior tooth in relation to the reference line;

determine the dental treatment difficulty of the initial to subsequent position based on the average change in position; and adjust a dental treatment plan based on a comparison of the dental treatment difficulty and a provider skill level.

17. The system of claim 16, wherein the dental treatment difficulty, a type of dental treatment, and a duration of dental treatment are adjusted based on the adjusted dental treatment plan.

18. The system of claim 16, wherein the posterior tooth is a molar.

19. The system of claim 16, wherein the processor coupled to the memory further executes the computer-readable instructions to determine the dental treatment difficulty based on a calculated anterior-posterior correction dental treatment plan.

20. The system of claim 16, further comprising a display module configured to display, via a user interface, at least one of the change in position, the projected changes, the average change in position, the dental treatment difficulty, and the adjusted dental treatment plan.

* * * * *